United States Patent [19]

Karasawa et al.

[11] Patent Number: 5,268,503
[45] Date of Patent: Dec. 7, 1993

[54] PROCESS FOR PRODUCING α,β-UNSATURATED CARBOXYLIC ACID ESTERS

[75] Inventors: Minato Karasawa; Sinji Tokunoh; Masamitsu Inomata; Takeshi Hiraiwa; Hiroharu Kageyama; Kanemitsu Miyama, all of Mobara, Japan

[73] Assignee: Mitsui Toatsu Chemicals, Incorporated, Tokyo, Japan

[21] Appl. No.: 29,419

[22] Filed: Mar. 9, 1993

[30] Foreign Application Priority Data

Mar. 16, 1992 [JP] Japan .................................. 4-057869

[51] Int. Cl.$^5$ ............................................... C07C 67/20
[52] U.S. Cl. ....................................... 560/215; 560/205
[58] Field of Search ............................... 560/215, 205

[56] References Cited

U.S. PATENT DOCUMENTS 3,418,359 12/1968 Barie et al. ........................... 560/205
4,950,788 8/1990 Farrar et al. ......................... 560/215
4,973,739 11/1990 Nagasawa et al. ................... 560/215
4,990,651 2/1991 Ikarashi et al. ...................... 560/215
5,087,737 2/1992 Higuchi et al. ...................... 560/215

FOREIGN PATENT DOCUMENTS 3141216 12/1978 Japan .
3144524 12/1978 Japan .
4055517 5/1979 Japan .
364597 3/1973 U.S.S.R. .
1004352 3/1983 U.S.S.R. .
2086892 5/1982 United Kingdom .

Primary Examiner—Paul J. Killos
Attorney, Agent, or Firm—Burns, Doane, Swecker & Mathis

[57] ABSTRACT

α,β-Unsaturated carboxylic acid esters are produced by a catalytic reaction of α,β-unsaturated carboxylic acids and/or α,β-unsaturated carboxylic acid amides with aliphatic alcohols in the presence of a solid acid catalyst comprising zirconium oxide, titanium oxide or a composite oxide thereof containing phosphorus.

12 Claims, 1 Drawing Sheet

PROCESS FOR PRODUCING α,β-UNSATURATED CARBOXYLIC ACID ESTERS

BACKGROUND OF THE INVENTION

1. Field of the Invention

The present invention relates to a process for producing an α,β-unsaturated carboxylic acid ester, and more particularly, to a process for producing an α,β-unsaturated carboxylic acid ester by reacting an α,β-unsaturated carboxylic acid and/or an α,β-unsaturated carboxylic acid amide with an aliphatic alcohol in the presence of a solid acid as a catalyst.

An α,β-unsaturated carboxylic acid ester is industrially very useful as a starting material for synthetic resins. In particular, methyl methacrylate is a starting material for poly(methyl methacrylate) which is excellent in weatherability and transparency.

2. Description of the Related Art

Heretofore, an α,β-unsaturated carboxylic acid ester, for example, methyl methacrylate, has been produced by treating acetone cyanohydrin with concentrated sulfuric acid to form methacrylamide sulfate and esterifying it with methanol.

This method has been used for the industrial production, but this process has various drawbacks such as corrosion of the apparatus material with the concentrated sulfuric acid and formation of a large amount of ammonium sulfate of a low value as a by-product.

On the contrary, Japanese Patent Publication No. Sho 63-63537 (U.S. Pat. No. 4,464,539) discloses a process for producing an α,β-unsaturated carboxylic acid ester from cyanohydrin without using sulfuric acid.

According to this method, an α-hydroxycarboxylic acid amide produced by hydration of the cyanohydrin is brought into contact with a first step solid acid catalyst in the presence of water, and then the resulting reaction mixture containing an α,β-unsaturated carboxylic acid and/or an α,β-unsaturated carboxylic acid amide is brought into contact with a second step solid acid catalyst together with an aliphatic alcohol to produce an α,β-unsaturated carboxylic acid ester.

In this method, as representative solid acid catalysts, there are used a catalyst containing a phosphoric acid salt such as lanthanum phosphate, cerium phosphate and the like in the first step and a catalyst containing a phosphate or oxide of titanium or zirconium in the second step.

As a result, an α,β-unsaturated carboxylic acid ester can be produced in a 80-89 mole % yield without forming ethers as by-broducts by a dehydration reaction of the aliphatic alcohol.

However, when an α,β-unsaturated carboxylic acid ester is produced by the above-mentioned method, in addition to the end product, α,β-unsaturated carboxylic acid ester, there are formed various by-products due to the action of the second step solid acid catalyst.

The by-products include alkylamines produced by the dehydration reaction of ammonia formed in the first and the second steps with the starting material, aliphatic alcohol, and N-alkyl α,β-unsaturated carboxylic acid amides produced by the dehydration reaction of the α,β-unsaturated carboxylic acid and/or α,β-unsaturated carboxylic acid amide formed in the first step with the above-mentioned alkylamines and/or aliphatic alcohol.

The yield of the by-products such as alkylamines and N-alkyl α,β-unsaturated carboxylic acid amides is about 2-9 mole % though it varies depending on the type of the second step solid acid catalyst, the reaction temperature and the like.

The formation of such by-products not only makes complicated the separation and purification steps for the α,β-unsaturated carboxylic acid ester and the recirculation step of unreacted α,β-unsaturated carboxylic acid and the like, but makes lower the economical efficiency of the process itself for producing the α,β-unsaturated carboxylic acid ester depending on the economical values and demands for the alkylamines and N-alkyl α,β-unsaturated carboxylic acid amides.

SUMMARY OF THE INVENTION

An object of the present invention is to provide a process for producing an α,β-unsaturated carboxylic acid ester substantially free from the formation of by-products.

Another object of the present invention is to provide a process for producing an α,β-unsaturated carboxylic acid ester in good yield.

According to the present invention, there is provided a process for producing an α,β-unsaturated carboxylic acid ester which comprises a catalytic reaction of at least one member selected from the group consisting of α,β-unsaturated carboxylic acids and α,β-unsaturated carboxylic acid amides represented by the general formula (1),

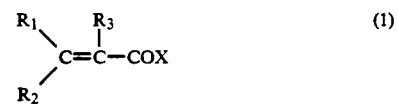

where $R_1$, $R_2$ and $R_3$ are independently selected from the group consisting of hydrogen and alkyl having 1-4 carbon atoms, and X is hydroxy or amino with an aliphatic alcohol in the presence of a solid acid catalyst, said solid acid catalyst being selected from the group consisting of zirconium oxide containing phosphorus, titanium oxide containing phosphorus, and a composite oxide of zirconium oxide and titanium oxide containing phosphorus, and the atomic ratio of phosphorus to zirconium and/or titanium being 0.0001-0.3.

DESCRIPTION OF THE PREFERRED EMBODIMENTS

Figure 1:
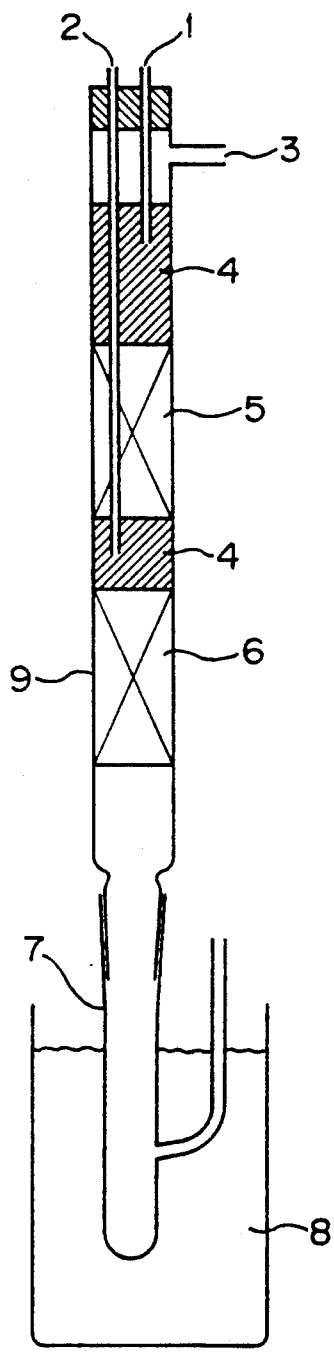
FIG. 1 shows schematically a cross sectional view of a reactor used in the working examples in this invention and the comparative examples.

In the present invention, there may be used an α,β-unsaturated carboxylic acid and/or an α,β-unsaturated carboxylic acid amide represented by the general formula (1),

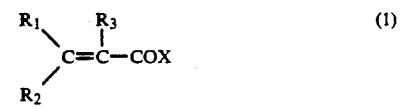

where $R_1$, $R_2$ and $R_3$ are independently selected from the group consisting of hydrogen and alkyl having 1-4 carbon atoms, and X is hydroxy or amino as one of the starting materials.

Exemplary suitable $\alpha,\beta$-unsaturated carboxylic acids and amides include:
acrylic acid,
acrylamide,
methacrylic acid,
methacrylamide,
$\beta$-methylacrylic acid,
$\beta$-methylacrylamide,
$\alpha,\beta$-dimethylacrylic acid,
$\alpha,\beta$-dimethylacrylamide,
$\beta,\beta$-dimethylacrylic acid,
$\beta,\beta$-dimethylacrylamide,
$\beta$-ethylacrylic acid, and
$\beta$-ethylacrylamide.

The $\alpha,\beta$-unsaturated carboxylic acid and/or $\alpha,\beta$-unsaturated carboxylic acid amide may be used separately from the other starting material, an aliphatic alcohol, or as a solution in the aliphatic alcohol or an aqueous aliphatic alcohol solution.

In the present invention, the above-mentioned $\alpha,\beta$-unsaturated carboxylic acid and/or $\alpha,\beta$-unsaturated carboxylic acid amide may be prepared by known methods such as those disclosed in Japanese Patent Publication No. Sho 63-10940 (U.S. Pat. No. 4,464,539) and Japanese Patent Publication No. Hei 3-13213.

For example, according to the method of Japanese Patent Publication No. Sho 63-10940 (U.S. Pat. No. 4,464,539), $\alpha$-hydroxycarboxylic acid amide obtained by the hydration reaction of cyanohydrin is preferably brought into contact with a solid acid catalyst in the presence of water to give a reaction mixture containing an $\alpha,\beta$-unsaturated carboxylic acid and/or an $\alpha,\beta$-unsaturated carboxylic acid amide.

As $\alpha$-hydroxycarboxylic acid amides, there may be mentioned lactic amide, $\alpha$-hydroxybutyramide, $\alpha$-hydroxyisobutyramide, and $\alpha$-hydroxyvaleramide, $\alpha$-hydroxyisovaleramide, and $\alpha$-methyl-$\alpha$-hydroxybutyramide.

As solid acid catalysts, there may be used catalysts containing phosphoric acid salts such as lanthanum phosphate and cerium phosphate.

According to the method of Japanese Patent Publication No. Hei 3-13213, an aqueous solution of $\alpha$-hydroxyisobutyramide obtained by hydration of acetone cyanohydrin is brought into contact with a solid acid catalyst to produce a reaction mixture containing methacrylic acid and methacrylamide. As a solid acid catalyst, there is used a catalyst containing a phosphoric acid salt such as magnesium primary phosphate or a sulfate such as cadmium sulfate.

Exemplary suitable aliphatic alcohols as a starting material in the present invention include:
methyl alcohol,
ethyl alcohol,
n-propyl alcohol,
i-propyl alcohol,
i-butyl alcohol,
ethylene glycol,
ethylene glycol monomethyl ether,
propylene glycol monomethyl ether,
and the like,
and substituted aliphatic alcohols.

An appropriate aliphatic alcohol may be selected from these alcohols depending on the type of the end product.

As solid acid catalysts of the present invention, there may be used such catalyst producible by dispersing properly phosphorus in zirconium oxide, titanium oxide or a composite oxide of zirconium oxide and titanium oxide. In these oxides or composite oxide, the atomic ratio of phosphorus (designated as "P") to zirconium and/or titanium (designated as "M"), that is, (P/M) is 0.0001-0.3, preferably 0.001-0.2 though it varies depending on the specific surface area ($m^2/g$) of the oxide or composite oxide.

When the atomic ratio (P/M) is less than 0.0001, the yield of the end product, $\alpha,\beta$-unsaturated carboxylic acid ester is markedly lowered. When the atomic ratio exceeds 0.3, the yield of by-products such as alkylamines and N-alkyl $\alpha,\beta$-unsaturated carboxylic acid amides disadvantageously increases.

As phosphorus components, there may be mentioned:
phosphoric acid,
ammonium dihydrogen phosphate,
diammonium hydrogen phosphate,
triammonium phosphate;
phosphoric acid esters such as
trimethyl phosphate,
triethyl phosphate,
tributyl phosphate,
triphenyl phosphate,
and the like;
phosphorus hydride,
phosphorus bromide,
phosphorus chloride,
phosphorus oxychloride,
and the like.

Among them, from the standpoint of easy handling, there is preferably mentioned:
phosphoric acid,
ammonium dihydrogen phosphate,
diammonium hydrogen phosphate,
triammonium phosphate,
trimethyl phosphate, and
triethyl phosphate.

In the following preparation of the catalyst, seemingly these phosphorus compounds react with hydroxide or oxide of zirconium and/or titanium and are partly fixed to the surface as phosphoric acid, zirconium phosphate and/or titanium phosphate, which are then calcined. As a result, these become stable active points.

In the present invention, zirconium oxide containing phosphorus can be prepared from the above-mentioned phosphorus compound, zirconium hydroxide and/or zirconium oxide by using a known catalyst preparation method such as a kneading method, a soaking method, a chemical vapor deposition or the like.

Alternatively, a co-precipitation method or kneading method is used to prepare zirconium hydroxide and/or zirconium oxide carried on a carrier such as silica, alumina, silica-alumina and the like and then a soaking method, chemical vapor deposition method or the like is employed to combine a phosphorus compound with said zirconium compound carried on a carrier.

In addition, a titanium oxide or a composite oxide of titanium oxide and zirconium oxide containing phosphorus can be prepared by a method similar to that as above using the above-mentioned phosphorus compound and titanium hydroxide and/or titanium oxide, or a mixture of titanium hydroxide and/or titanium oxide and zirconium hydroxide and/or zirconium oxide.

The amount of the starting material in the present invention is not particularly critical. For example, when the starting material is $\alpha$-hydroxycarboxylic acid amide, the amount of water is usually 0-200 moles, preferably 1–50 moles per 1 mole of α-hydroxycarboxylic acid amide.

The amount of aliphatic alcohol is usually 1–200 moles, preferably 1–50 moles per 1 mole of the resulting α,β-unsaturated carboxylic acid and/or α,β-unsaturated carboxylic acid amide contained in the reaction mixture.

In the present invention, the reaction may be carried out in a vapor phase or liquid phase as far as the starting materials can be brought into contact with the solid acid catalyst, and a vapor phase or a vapor-liquid mixed phase is preferable.

The reaction may be carried out by a fixed bed system, a fluidized bed system or any other optional system.

The reaction temperature is usually 150–500° C., preferably 200–450° C.

The reaction pressure is usually atmospheric pressure, but may be higher or lower than atmospheric pressure.

Feeding speeds of the starting materials, i.e. α,β-unsaturated carboxylic acid and/or α,β-unsaturated carboxylic acid amide and aliphatic alcohol may be varied widely depending on type of catalyst, reaction temperature and the like, but usually a liquid hourly space velocity (LHSV) in the range of 0.005–10 $hr^{-1}$ is sufficient.

Further, in carrying out the reaction, the starting material may be mixed with an inert gas such as a nitrogen gas and then brought into contact with the catalyst layer.

The catalyst may be subjected to a pre-treatment by feeding ammonia or aqueous ammonia to the catalyst layer and then the reaction may be started though such pretreatment is not always necessary.

According to the present invention, an α,β-unsaturated carboxylic acid ester can be obtained in good yield while suppressing the formation of by-products such as alkylamines and N-alkyl α,β-unsaturated carboxylic acid amides as far as possible, or substantially completely, for a long period of time in the process for producing an α,β-unsaturated carboxylic acid ester starting from an α,β-unsaturated carboxylic acid and/or an α,β-unsaturated carboxylic acid amide.

For example, an α,β-unsaturated carboxylic acid ester can be produced in a 72–94 mole % for more than 10 days substantially without forming by-products such as the amines and amides.

In the following, the present invention is explained referring to examples and comparative examples.

In all of the examples and comparative examples, there was used a reaction tube 9 having two steps of catalyst layers in FIG. 1.

The first step catalyst layer 5 was packed with a LaPO$_4$ catalyst prepared as shown below in the procedures of Examples 1–16, Examples 28–39, Comparative Examples 1–9 and Comparative Examples 14–20, and with melted alumina balls in place of catalyst in Examples 17–27 and Comparative Examples 10–13.

In the following, "%" is by weight unless otherwise specified.

PREPARATION OF THE FIRST STEP CATALYST

Lanthanum oxide (La$_2$O$_3$) 21.2 g (0.065 mole) was completely dissolved in an aqueous solution of nitric acid, heated and concentrated to form lanthanum nitrate.

Water was added thereto to form a 400 ml of an aqueous solution of lanthanum nitrate.

Then, to said aqueous solution of lanthanum nitrate was added 100 ml of an aqueous solution containing disodium hydrogenphosphate (Na$_2$HPO$_4$) 20.3 g (0.143 mole) and a white precipitate was formed. The resulting solution was stirred at 80° C. for one hour, and the white precipitate was sufficiently washed with water by decantation method, separated by filtration and then washed with water.

The resulting white precipitate was dried at 120° C., calcined in an air stream at 400° C. for 6 hours, and molded into particles of 10–16 mesh to prepare a lanthanum phosphate (LaPO$_4$) catalyst.

The indication "lanthanum phosphate (LaPO$_4$)" does not always show the structure of the phosphoric acid salt contained in the catalyst, but the atomic ratio of lanthanum to phosphorus in the phosphoric acid salt.

EXAMPLE 1

The second step catalyst was prepared as shown below. Zirconium oxychloride (ZrOCl$_2$.8H$_2$O) 36.1 g (0.112 mole) was dissolved in water 50 ml and then added with stirring to a solution formed by dissolving sodium hydroxide (NaOH) 9.84 g (0.246 mole) in water 200 ml and heated to 80° C. to form white precipitate.

After stirring the resulting solution for one hour, the white precipitate was sufficiently washed with water by a decantation method, filtered, further washed with water and dried at 100° C. to obtain zirconium hydroxide (Zr(OH)$_4$) 16.9 g. Then the resulting zirconium hydroxide 15.9 g (0.100 mole) was ground for 3 hours by an automatic mortar. To the zirconium hydroxide thus ground was added diammonium hydrogenphosphate ((NH$_4$)$_2$HPO$_4$) 0.46 g (0.0035 mole) finely divided by an agate mortar, ground and mixed for 10 hours.

The resulting mixture was allowed to stand in air at 200° C. for 5 hours, then calcined in air at 400° C. for 6 hours, and molded into particles of 10–16 mesh to prepare zirconium oxide containing phosphorus of P/Zr=0.035 (hereinafter referred to as "P-ZrO$_2$").

In a Pyrex reaction tube 9 of 12 mm in inner diameter as shown in FIG. 1, a second step catalyst layer 6 was composed of 5 ml of the above-mentioned P-ZrO$_2$ catalyst, a first step catalyst layer 5 was composed of 5 ml of the above-mentioned LaPO$_4$ catalyst, and a vaporization portion 4 was packed with melted alumina balls of 3 mm in diameter.

This reaction tube was fixed to an electric furnace capable of controlling independently the temperature of the first step catalyst layer and the temperature of the second step catalyst layer, and was connected with a reaction fluid receiver 7 cooled with dry ice trap 8 as illustrated in FIG. 1.

Then, a nitrogen gas was introduced from a carrier gas feeding pipe 3 at the top portion of the reaction tube and fed at a rate of 10 ml/min (GHSV 120 hr$^{-1}$) to the catalyst layer, while the catalyst layer temperature was raised to 275° C. at the first step and 330° C. at the second step.

Methyl alcohol was fed at a rate of 8.5 ml/hr (LHSV 1.7 hr$^{-1}$) through a starting material feeding pipe 2 while a 36% aqueous solution of α-hydroxyisobutyramide was fed at a rate of 4.4 ml/hr (LHSV 0.88 hr$^{-1}$) through a starting material feeding pipe 1.

During 3–4 hours after beginning the feed of starting materials, reaction fluid fraction for this one hour was captured by means of dry ice trap 8 and analyzed by gas chromatography. The yield of methyl methacrylate (hereinafter referred to as "MMA") based on the starting material, α-hydroxyisobutyramide, was 91.5 mole %.

Other than MMA, only acetone was formed as a by-product in a 3.5 mole % yield based on α-hydroxyisobutyramide, but methylamine, dimethylamine, trimethylamine, N-methylmethacrylamide and N,N-dimethylmethacrylamide were not detected.

EXAMPLES 2-12 AND COMPARATIVE EXAMPLES 1-6

The procedure of Example 1 was repeated except that the atomic ratio (P/Zr) of phosphorus to zirconium in P-$ZrO_2$ as the second step catalyst and the reaction temperature at the second step were changed. The P/Zr, reaction temperatures and yields of reaction products are shown in Table 1.

COMPARATIVE EXAMPLES 7 AND 8

The procedure of Example 1 was repeated except that the other second step catalyst species was used and the reaction temperature of the second step was changed. The other second step catalyst was prepared as shown below.

Zirconium oxychloride ($ZrOCl_2.8H_2O$) 36.1 g (0.112 mole) was dissolved in 50 ml of water, and to the resulting solution was added 200 ml of an aqueous solution containing disodium hydrogenphosphate ($Na_2HPO_4$) 31.8 g (0.224 mole) to form a white precipitate. The resulting mixture was stirred at 80° C. for one hour, and the white precipitate was sufficiently washed with water by a decantation method, filtered, further washed with water, and dried at 120° C. to obtain zirconium phosphate ($Zr(HPO_4)_2$) 30.1 g.

The resulting zirconium phosphate was calcined at 500° C. for 6 hours in air, and molded into particles of 10-16 mesh to form a zirconium phosphate ($Zr(HPO_4)_2$) of P/Zr=2.00.

The indication "zirconium phosphate ($Zr(HPO_4)$)" does not always show the structure of the phosphoric acid salt contained in the catalyst, but the atomic ratio of zirconium to phosphorus in the phosphoric acid salt.

Table 1 shows the P/Zr, reaction temperatures and yields of reaction products.

EXAMPLE 13

The procedure of Example 1 was repeated except that the other second step catalyst species was used.

The other second step catalyst was prepared as shown below.

Zirconium oxychloride ($ZrOCl_2.8H_2O$) 36.1 g (0.112 mole) was dissolved in 50 ml of water. The resulting solution was added with stirring to a solution prepared by dissolving sodium hydroxide (NaOH) 9.84 g (0.246 mole) in 200 ml of water and heating to 80° C. to produce white precipitate.

After stirring for one hour, the white precipitate was sufficiently washed with water by a decantation method, filtered, washed with water again and dried at 100° C. The product thus dried was calcined in air at 330° C. for 4 hours to obtain zirconium oxide ($ZrO_2$) 13.0 g.

The resulting zirconium oxide 10.0 g (0.081 mole) was added to 50 ml of an aqueous solution containing trimethyl phosphate ($(CH_3O)_3PO_4$) 3.5 g (0.025 mole) and soaked at 80° C. for 6 hours. Then, the product was washed with water, filtered, dried at 100° C., and calcined in air at 400° C. for 6 hours to prepare a zirconium oxide (P-$ZrO_2$) catalyst containing phosphorus of P/Zr=0.035. The phosphorus content in zirconium oxide was determined by a fluorescent X-ray method.

Table 2 shows the yields of reaction products.

EXAMPLE 14

The procedure of Example 1 was repeated except that the other second step catalyst species was used.

The other second step catalyst was prepared as shown below.

Zirconium oxychloride ($ZrOCl_2.8H_2O$) 36.1 g (0.112 mole) was dissolved in 50 ml of water, and the resulting solution was added with stirring to a solution prepared by dissolving sodium hydroxide (NaOH) 9.84 g (0.246 mole) in 200 ml of water and heating to 80° C. to form a white precipitate.

After stirring for one hour, the resulting white precipitate was sufficiently washed with water by a decantation method, filtered, washed with water again and dried at 100° C.

The product thus dried was calcined in air at 330° C. for 4 hours to obtain zirconium oxide ($ZrO_2$) 13 g.

Then the resulting zirconium oxide 10.0 g (0.081 mole) was added to 50 ml of an aqueous solution containing 85% phosphoric acid 0.58 g (0.005 mole) and soaked at room temperature for 120 hours. The resulting product was washed with water, filtered, dried at 100° C. and calcined in air at 400° C. for 6 hours to obtain a P-$ZrO_2$ catalyst of P/Zr=0.035.

The phosphorus content in the resulting zirconium oxide was determined by a fluorescent X-ray method.

Table 2 shows the yields of the reaction product.

EXAMPLE 15

The procedure of Example 1 was repeated except that the other second step catalyst species was used.

The other second step catalyst was prepared as shown below.

Zirconium oxychloride ($ZrOCl_2.8H_2O$) 36.1 g (0.112 mole) was dissolved in 50 ml of water, and the resulting solution was added with stirring to a solution prepared by dissolving sodium hydroxide (NaOH) 9.84 g (0.246 mole) in 200 ml of water and heating to 80° C. to form a white precipitate.

After stirring for one hour, the white precipitate was sufficiently washed with water by a decantation method, filtered, washed with water again, and dried at 100° C. The product thus dried was calcined in air at 330° C. for 4 hours to obtain zirconium oxide ($ZrO_2$) 13.0 g.

Then the resulting zirconium oxide 10.0 g (0.081 mole) was added to 50 ml of an aqueous solution containing diammonium hydrogenphosphate (($NH_4)_2HPO_4$) 1.3 g and soaked at room temperature for 72 hours. The resulting product was washed with water, filtered, and dried at 100° C., calcined in air at 400° C. for 6 hours to prepare a P-$ZrO_2$ catalyst of P/Zr=0.035.

The phosphorus content in zirconium oxide was determined by a fluorescent X-ray method.

Table 2 shows the yield of reaction products.

EXAMPLE 16

The procedure of Example 1 was repeated except that the other second step catalyst species was used.

Said second step catalyst was prepared as shown below.

Zirconium oxychloride ($ZrOCl_2 \cdot 8H_2O$) 7.9 g (0.024 mole) was dissolved in 30 ml of water, and the resulting solution was added to 7.0 g of silica (SILICA 951W, trade name, supplied by Fuji Davison Co.) treated at 1000° C. for 5 hours. The resulting mixture was vaporized to driness and calcined in air at 400° C. for 3 hours to obtain a silica carrying 3% zirconium oxide.

The resulting silica carrying zirconium oxide 9.0 g (corresponding to 0.0022 mole of $ZrO_2$) was added to 50 ml of an aqueous solution containing trimethyl phosphate (($CH_3O$)$_3PO_4$) 0.5 g (0.0036 mole) and soaked at 80° C. for 6 hours. Then, the product was washed with water, filtered, dried at 100° C., and calcined in air at 400° C. for 6 hours to obtain a silica catalyst carrying zirconium oxide containing phosphorus of P/Zr=0.035.

The phosphorus content in zirconium oxide was determined by a fluorescent X-ray method.

Table 2 shows the yield of the reaction product.

COMPARATIVE EXAMPLE 9

The procedure of Example 1 was repeated except that the other second step catalyst species was used.

Said second step catalyst was prepared as shown below.

The zirconium phosphate ($Zr(HPO_4)_2$) catalyst of P/Zr=2.00 obtained in Comparative Example 7, 0.41 g (0.0014 mole) was finely divided by using an agate mortar.

On the other hand, zirconium oxide ($ZrO_2$) obtained in Example 13, 10.0 g (0.081 mole) was ground by an automatic mortar for 3 hours. To the zirconium oxide thus ground was added the above-mentioned finely divided zirconium phosphate and ground and mixed for 10 hours.

The resulting mixture was calcined in air at 400° C. for 6 hours and molded into particles of 10–16 mesh to prepare a P-$ZrO_2$ catalyst of P/Zr=0.035.

The phosphorus content in the zirconium oxide was measured by a fluorescent X-ray method.

Table 2 shows the yield of the reaction product.

EXAMPLE 17

The procedure of Example 1 was repeated except that the first step catalyst layer portion 5 was packed with melted alumina balls of 3 mm in diameter in place of the catalyst, the second step catalyst layer 6 was packed with a P-$ZrO_2$ catalyst (P/Zr=0.035) obtained in Example 13, and the starting materials and amounts thereof were changed as shown below.

In place of a 36% aqueous solution of α-hydroxyisobutyramide and methyl alcohol, there was used a 20% solution of methacrylamide in methyl alcohol as starting materials, and this solution was fed through starting material feeding pipe 1 at a rate of 3.4 ml/hr (LHSV 0.68 hr$^{-1}$) while nothing was fed through starting material feeding pipe 2.

Table 3 shows the yield of the reaction product.

EXAMPLES 18–21

The procedure of Example 17 was repeated except that the starting material and concentration thereof were changed. Table 3 shows the starting materials, concentrations thereof and yields of the reaction products.

EXAMPLE 22

The procedure of Example 1 was repeated except that the first step catalyst layer 5 was packed with melted alumina balls of 3 mm in diameter in place of the catalyst and the starting materials, the amounts fed and the reaction time were changed as shown below.

As starting material, a 20% solution of methacrylamide in methyl alcohol was used in place of a 36% aqueous solution of α-hydroxyisobutyramide and methyl alcohol and fed through starting material feeding pipe 1 at a rate of 3.4 ml/hr (LHSV 0.68 hr$^{-1}$) while nothing was fed through starting material feeding pipe 2. During 3–4 hours and 240–241 hours after beginning to feed the starting material, the reaction fluid fraction corresponding to respective one hour was captured by dry ice trap 8 and analyzed by gas chromatography.

Table 4 shows the yield of the main reaction product (MMA) and productivity of the catalyst.

EXAMPLES 23–27 AND COMPARATIVE EXAMPLES 10–13

The procedure of Example 22 was repeated except that the atomic ratio of phosphorus to zirconium (P/Zr) of P-$ZrO_2$ as the second step catalyst was changed. Table 4 shows P/Zr, yield of the main reaction product (MMA) and productivity of catalyst.

EXAMPLE 28

The procedure of Example 1 was repeated except that P-$TiO_2$ was used in place of P-$ZrO_2$ as a second step catalyst species.

The second step catalyst was prepared as shown below.

Titanium chloride ($TiCl_4$) 40.1 g (0.211 mole) was dropwise added to and dissolved in 80 ml of ice-cooled water, and water was added thereto. To the resulting aqueous solution was gradually dropwise added a 28% aqueous ammonia until the aqueous solution became pH 7, followed by stirring at 80° C. for one hour.

The resulting precipitate was sufficiently washed with water by a decantation method, filtered, washed with water again, and dried at 100° C. to obtain 20.2 g of titanium hydroxide ($Ti(OH)_4$).

The resulting titanium hydroxide 11.6 g (0.100 mole) was ground with an automatic mortar for 3 hours. To the titanium hydroxide thus ground was added diammonium hydrogenphosphate (($NH_4)_2HPO_4$) finely divided by using an agate mortar, 0.46 g (0.0035 mole), ground and mixed for 10 hours.

The resulting mixture was allowed to stand in air at 200° C. for 2 hours, calcined in air at 400° C. for 6 hours, and molded into particles of 10–16 mesh to produce a catalyst of titanium oxide containing phosphorus (hereinafter referred to as "P-$TiO_2$") at a ratio of P/Ti=0.035.

Table 5 shows P/Ti, reaction temperature and yield of reaction products.

EXAMPLES 29–32 AND COMPARATIVE EXAMPLES 14–17

The procedure of Example 28 was repeated except that the atomic ratio of phosphorus to titanium of P-$TiO_2$ as a second step catalyst and the second step reaction temperature were changed.

Table 5 shows each P/Ti, reaction temperature and yield of reaction product.

EXAMPLE 33

The procedure of Example 1 was repeated except that the second step catalyst species, P-$ZrO_2$, was replaced with P-$ZrTiO_2$.

The second step catalyst, P-$ZrTiO_2$, was prepared as shown below.

Zirconium hydroxide ($Zr(OH)_4$) obtained in Example 1, 12.7 g (0.080 mole) and titanium hydroxide ($Ti(OH)_4$) obtained in Example 28, 1.6 g (0.020 mole), were ground for 3 hours by an automatic mortar.

To the mixture thus ground was added diammonium hydrogenphosphate (($NH_4)_2HPO_4$) finely divided by an agate mortar, 0.46 g (0.0035 mole), ground and mixed for 10 hours.

The resulting mixture was allowed to stand in air at 200° C. for 5 hours, calcined in air at 400° C. for 6 hours and molded into particles of 10-16 mesh to obtain a composite oxide catalyst containing phosphorus (hereinafter referred to as "P-$ZrTiO_2$") of P/(Zr+Ti)=0.035 and Zr/Ti=4.0.

Table 6 shows P/(Zr+Ti), Zr/Ti, reaction temperature, and yield of reaction product.

EXAMPLES 34-39 AND COMPARATIVE EXAMPLES 18-22

The procedure of Example 33 was repeated except that P/(Zr+Ti), Zr/Ti of P-$ZrTiO_2$, a second step catalyst, and the second step reaction temperature were changed.

Table 6 shows P/(Zr+Ti), Zr/Ti, reaction temperature, and yield of reaction product.

TABLE 1

| | Second step catalyst layer | | Yield (mol %) | | |
|---|---|---|---|---|---|
| | P/Zr of P—$ZrO_2$ | Temperature (°C.) | MMA | Amines (*1) | Amides (*2) |
| Example 1 | 0.0350 | 330 | 91.5 | 0.0 | 0.0 |
| Example 2 | 0.0007 | 300 | 83.2 | 0.0 | 0.0 |
| Example 3 | 0.0007 | 330 | 87.5 | 0.0 | 0.0 |
| Example 4 | 0.0070 | 300 | 88.5 | 0.0 | 0.0 |
| Example 5 | 0.0070 | 330 | 93.8 | 0.0 | 0.0 |
| Example 6 | 0.0140 | 300 | 91.2 | 0.0 | 0.0 |
| Example 7 | 0.0140 | 330 | 93.5 | 0.0 | 0.0 |
| Example 8 | 0.0350 | 300 | 91.3 | 0.0 | 0.0 |
| Example 9 | 0.140 | 300 | 93.5 | 0.0 | 0.0 |
| Example 10 | 0.140 | 330 | 91.1 | 0.2 | 0.2 |
| Example 11 | 0.250 | 300 | 94.0 | 0.3 | 0.2 |
| Example 12 | 0.250 | 330 | 90.3 | 1.9 | 1.7 |
| Comparative Example 1 | 0.0000 | 300 | 65.4 | 0.0 | 0.0 |
| Comparative Example 2 | 0.0000 | 350 | 80.0 | 0.0 | 0.0 |
| Comparative Example 3 | 0.350 | 300 | 90.8 | 3.5 | 3.2 |
| Comparative Example 4 | 0.350 | 330 | 85.7 | 7.2 | 6.9 |
| Comparative Example 5 | 0.400 | 300 | 90.5 | 4.0 | 3.3 |
| Comparative Example 6 | 0.400 | 330 | 83.4 | 8.8 | 7.9 |
| Comparative Example 7 | 2.00 | 280 | 89.0 | 3.2 | 2.0 |
| Comparative Example 8 | 2.00 | 300 | 83.5 | 5.2 | 7.3 |

(*1) Although methylamine, dimethylamine and trimethylamine are not directly produced from α-hydroxyisobutyramide, it is assumed for convenience that the total amount of these products per the feed amount of α-hydroxyisobutyramide is the yield of amines (mol %).

(*2) The yield of amides (mol %) is defined as the total amount of produced N-methylmethacrylamide and N,N-dimethylmethacrylamide per the feed amount of α-hydroxyisobutyramide.

TABLE 2

| | Preparation of second step catalyst | | | Yield (mol %) | | |
|---|---|---|---|---|---|---|
| | Phosphorus compound | Zirconium compound | Carrier | MMA | Amines (*1) | Amides (*2) |
| Example 1 | Diammonium hydrogen-phosphate | Hydroxide | None | 91.5 | 0.0 | 0.0 |
| Example 13 | Trimethyl phosphate | Oxide | None | 94.4 | 0.0 | 0.0 |
| Example 14 | Phosphoric acid | Oxide | None | 93.5 | 0.0 | 0.0 |
| Example 15 | Diammonium hydrogen-phosphate | Oxide | None | 93.9 | 0.0 | 0.0 |
| Example 16 | Trimethyl phosphate | Oxide | Silica | 92.1 | 0.1 | 0.1 |
| Comparative Example 9 | Zirconium phosphate | Oxide | None | 71.3 | 3.4 | 2.7 |

TABLE 3

| | Starting material | | | Yield (mol %) | | |
|---|---|---|---|---|---|---|
| | Type | Concentration % | mol % | Main product | Ester | Amines (*3) | Amides (*4) |
| Example 17 | Methacrylamide | 20 | 8.6 | MMA | 96.3 | 0.0 | 0.0 |
| | Methyl alcohol | 80 | 91.4 | | | | |
| Example 18 | Methacrylic acid | 15 | 5.9 | | | | |
| | Methacrylamide | 5 | 2.6 | MMA | 96.9 | 0.0 | 0.0 |
| | Methyl alcohol | 80 | 91.5 | | | | |
| Example 19 | Methacrylic acid | 5 | 1.7 | | | | |
| | Methacrylamide | 15 | 6.8 | MMA | 96.5 | 0.0 | 0.0 |
| | Methyl alcohol | 80 | 91.5 | | | | |

TABLE 3-continued

| | Starting material | | | | Yield (mol %) | |
|---|---|---|---|---|---|---|
| | Type | Concentration % | ration mol % | Main product | Ester | Amines (*3) | Amides (*4) |
| Example 20 | Methacrylamide | 15 | 8.7 | Ethyl methacrylate | 91.4 | 0.0 | 0.0 |
| | Ethyl alcohol | 85 | 91.3 | | | | |
| Example 21 | Methacrylamide | 10 | 3.5 | Ethylene glycol monomethacrylate | 72.0 | 0.0 | 0.0 |
| | Ethylene glycol | 45 | 21.8 | | | | |
| | Water | 45 | 74.7 | | | | |

(*3) Although alkylamines corresponding to aliphatic alcohols are not directly produced from methacrylic acid and/or methacrylamide, it is assumed for convenience that the total amount of these products per the feed amount of methacrylic acid and/or methacrylamide is the yield of amines (mol %).

(*4) The yield of amides (mol %) is defined as the total amount of produced N-alkylmethacrylamide and N,N-dialkylmethacrylamide corresponding to aliphatic alcohols per the feed amount of methacrylic acid and/or methacrylamide.

TABLE 4

| | Second step catalyst layer | | MMA Yield (mol %) | | Productivity of catalyst (*6) | |
|---|---|---|---|---|---|---|
| | P/Zr of P—ZrO$_2$ | Temperature (°C.) | 3–4 hrs | 240–241 hrs | MMA | Amides (*5) |
| Example 1 | 0.0350 | 330 | 91.5 | — | — | — |
| Example 22 | 0.0350 | 330 | 92.2 | 79.4 | 26.5 | 0.0 |
| Example 23 | 0.0007 | 330 | 89.1 | 71.6 | 24.8 | 0.0 |
| Example 24 | 0.0070 | 330 | 94.0 | 78.8 | 26.7 | 0.0 |
| Example 25 | 0.0140 | 330 | 94.3 | 79.2 | 26.8 | 0.0 |
| Example 26 | 0.140 | 330 | 93.8 | 77.3 | 26.4 | 0.1 |
| Example 27 | 0.250 | 330 | 93.1 | 78.2 | 26.4 | 0.6 |
| Comparative Example 10 | 0.0000 | 330 | 77.8 | 42.3 | 18.5 | 0.0 |
| Comparative Example 11 | 0.350 | 330 | 91.3 | 71.8 | 25.2 | 1.9 |
| Comparative Example 12 | 0.400 | 330 | 91.1 | 67.5 | 24.5 | 2.8 |
| Comparative Example 13 | 2.00 | 330 | 84.4 | 35.4 | 18.5 | 3.4 |

(*5) The total product amount is calculated assuming that the yield of amides of *2 is the yield of N-methylmethacrylamide.
(*6) The total amount of MMA or amides per unit amount of catalyst after 241 hours.

TABLE 5

| | Second step catalyst layer | | Yield (mol %) | | |
|---|---|---|---|---|---|
| | P/Ti of P—TiO$_2$ | Temperature (°C.) | MMA | Amines (*1) | Amides (*2) |
| Example 28 | 0.0350 | 330 | 91.5 | 0.0 | 0.0 |
| Example 29 | 0.0007 | 330 | 86.5 | 0.0 | 0.0 |
| Example 30 | 0.0070 | 330 | 92.8 | 0.0 | 0.0 |
| Example 31 | 0.0140 | 300 | 94.2 | 0.0 | 0.0 |
| Example 32 | 0.140 | 300 | 92.5 | 0.2 | 0.1 |
| Comparative Example 14 | 0.0000 | 350 | 81.3 | 0.0 | 0.0 |
| Comparative Example 15 | 0.350 | 300 | 87.8 | 4.5 | 3.5 |
| Comparative Example 16 | 0.400 | 300 | 86.3 | 7.8 | 6.3 |
| Comparative Example 17 | 0.500 | 300 | 82.3 | 8.2 | 7.1 |

TABLE 6

| | Second step catalyst layer | | | Yield (mol %) | | |
|---|---|---|---|---|---|---|
| | P/(Zr+Ti) of P—ZrTiO$_2$ | Zr/Ti | Temperature (°C.) | MMA | Amines (*1) | Amides (*2) |
| Example 33 | 0.0350 | 4.0 | 330 | 91.7 | 0.0 | 0.0 |
| Example 34 | 0.0350 | 0.5 | 330 | 92.5 | 0.0 | 0.0 |
| Example 35 | 0.0350 | 1.0 | 330 | 92.8 | 0.0 | 0.0 |
| Example 36 | 0.0350 | 2.0 | 300 | 92.2 | 0.0 | 0.0 |
| Example 37 | 0.0350 | 3.0 | 330 | 91.8 | 0.0 | 0.0 |
| Example 38 | 0.0070 | 4.0 | 300 | 85.2 | 0.0 | 0.0 |
| Example 39 | 0.0140 | 4.0 | 300 | 93.5 | 0.1 | 0.1 |
| Comparative Example 18 | 0.0000 | 1.0 | 350 | 84.0 | 0.0 | 0.0 |
| Comparative Example 19 | 0.0000 | 4.0 | 350 | 82.8 | 0.0 | 0.0 |
| Comparative Example 20 | 0.350 | 1.0 | 300 | 88.5 | 6.7 | 4.5 |
| Comparative | 0.350 | 4.0 | 330 | 89.1 | 4.2 | 3.8 |

TABLE 6-continued

| | Second step catalyst layer | | | Yield (mol %) | | |
|---|---|---|---|---|---|---|
| | P/(Zr+Ti) of P—ZrTiO$_2$ | Zr/Ti | Temperature (°C.) | MMA | Amines (*1) | Amides (*2) |
| Example 21 Comparative Example 22 | 0.400 | 4.0 | 300 | 87.7 | 5.6 | 4.7 |

What is claimed is:

1. A process for producing an $\alpha,\beta$-unsaturated carboxylic acid ester which comprises a catalytic reaction of at least one member selected from the group consisting of $\alpha,\beta$-unsaturated carboxylic acids and $\alpha,\beta$-unsaturated carboxylic acid amides represented by the general formula (1),

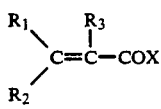

$$\begin{array}{c} R_1 \\ \phantom{R}\diagdown \\ \phantom{RR}C=C-COX \\ \diagup \phantom{RR} \\ R_2 \phantom{RRR} R_3 \end{array} \qquad (1)$$

where $R_1$, $R_2$ and $R_3$ are independently selected from the group consisting of hydrogen and alkyl having 1–4 carbon atoms, and X is hydroxy or amino, with an aliphatic alcohol in the presence of a solid acid catalyst, said solid acid catalyst being selected from the group consisting of zirconium oxide containing phosphorus, titanium oxide containing phosphorus, and a composite oxide of zirconium oxide and titanium oxide containing phosphorus, and the atomic ratio of phosphorus to zirconium and/or titanium being 0.0001–0.3.

2. The process according to claim 1 in which the atomic ratio of phosphorus to zirconium and/or titanium is 0.001–0.2.

3. The process according to claim 1 in which the solid acid catalyst is zirconium oxide containing phosphorus.

4. The process according to claim 1 in which the solid acid catalyst is titanium oxide containing phosphorus.

5. The process according to claim 1 in which the solid acid catalyst is a composite oxide of zirconium oxide and titanium oxide containing phosphorus.

6. The process according to claim 1 in which the solid acid catalyst is zirconium oxide containing phosphorus prepared from at least one member selected from the group consisting of phosphoric acid, ammonium dihydrogenphosphate, diammonium hydrogenphosphate, triammonium phosphate, trimethyl phosphate, and triethyl phosphate, and zirconium hydroxide and/or zirconium oxide.

7. The process according to claim 1 in which the solid acid catalyst is titanium oxide containing phosphorus prepared from at least one member selected from the group consisting of phosphoric acid, ammonium dihydrogenphosphate, diammonium hydrogenphosphate, triammonium phosphate, trimethyl phosphate, and triethyl phosphate, and titanium oxide and/or titanium hydroxide.

8. The process according to claim 1 in which the solid acid catalyst is a composite oxide of zirconium oxide and titanium oxide containing phosphorus prepared from at least one member selected from the group consisting of phosphoric acid, ammonium dihydrogenphosphate, diammonium hydrogenphosphate, triammonium phosphate, trimethyl phosphate, and triethyl phosphate, and zirconium hydroxide and/or zirconium oxide, and titanium hydroxide and/or titanium oxide.

9. The process according to claim 1 in which the at least one member is a mixture of methacrylic acid and methacrylamide.

10. The process according to claim 1 in which the at least one member is methacrylamide.

11. The process according to claim 1 in which the aliphatic alcohol is selected from the group consisting of methyl alcohol, ethyl alcohol, n-propyl alcohol, i-propyl alcohol, i-butyl alcohol and ethylene glycol.

12. The process according to claim 1 in which the aliphatic alcohol is methyl alcohol.

* * * * *